United States Patent
Scherze et al.

(10) Patent No.: US 7,635,575 B2
(45) Date of Patent: Dec. 22, 2009

(54) METHOD FOR CULTIVATING CELLS, PARTICULARLY HUMAN OR ANIMAL CELLS

(75) Inventors: Wilhelm Scherze, Spargelweg (DE); Josef Seidl, Aldersbach (DE)

(73) Assignee: PAN-Biotech GmbH, Aidenbach (DE)

(*) Notice: Subject to any disclaimer, the term of this patent is extended or adjusted under 35 U.S.C. 154(b) by 289 days.

(21) Appl. No.: 10/528,060

(22) PCT Filed: Sep. 16, 2002

(86) PCT No.: PCT/EP02/10357

§ 371 (c)(1),
(2), (4) Date: Mar. 15, 2005

(87) PCT Pub. No.: WO2004/033615

PCT Pub. Date: Apr. 22, 2004

(65) Prior Publication Data

US 2006/0003441 A1    Jan. 5, 2006

(51) Int. Cl.
| C12Q 1/02 | (2006.01) |
| C12M 3/00 | (2006.01) |
| C12N 5/00 | (2006.01) |
| C12M 1/34 | (2006.01) |
| C12M 5/08 | (2006.01) |

(52) U.S. Cl. ................ 435/29; 435/286.5; 435/287.1; 435/297.2; 435/297.5; 435/305.3; 435/325; 435/366

(58) Field of Classification Search .............. None
See application file for complete search history.

(56) References Cited

U.S. PATENT DOCUMENTS

| 3,836,335 | A | | 9/1974 | Eppes et al. |
| 3,895,741 | A | | 7/1975 | Nugent |
| 3,941,662 | A | | 3/1976 | Munder et al. |
| 4,175,860 | A | | 11/1979 | Bacus |
| 4,565,598 | A | | 1/1986 | Seymour |
| 4,629,686 | A | | 12/1986 | Gruenberg |
| 4,650,766 | A | | 3/1987 | Harm et al. |
| 4,810,658 | A | | 3/1989 | Shanks et al. |
| 4,839,292 | A | | 6/1989 | Cremonese |
| 4,974,952 | A | | 12/1990 | Focht |
| 4,999,298 | A | | 3/1991 | Wolfe et al. |
| 5,286,646 | A | | 2/1994 | Kearns et al. |
| 5,424,209 | A | * | 6/1995 | Kearney ............ 435/286.5 |
| 5,629,202 | A | | 5/1997 | Su et al. |
| 5,665,599 | A | | 9/1997 | Minuth |
| 5,700,632 | A | | 12/1997 | Critser et al. |
| 5,770,392 | A | | 6/1998 | Davies |
| 6,251,653 | B1 | | 6/2001 | Bramble |
| 6,329,195 | B1 | * | 12/2001 | Pfaller ............ 435/297.2 |
| 6,447,726 | B1 | * | 9/2002 | Delucas et al. ......... 422/99 |
| 6,468,788 | B1 | | 10/2002 | Marotzki |
| 6,498,862 | B1 | | 12/2002 | Pierson et al. |
| 6,586,235 | B1 | | 7/2003 | Banes |
| 6,630,343 | B1 | | 10/2003 | Bartenschlager |
| 6,656,449 | B1 | | 12/2003 | Serbedzija et al. |
| 6,673,595 | B2 | | 1/2004 | Barbera-Guillem |
| 6,673,620 | B1 | | 1/2004 | Loeffler et al. |
| 6,706,520 | B2 | | 3/2004 | Han et al. |
| 6,713,298 | B2 | | 3/2004 | McDevitt et al. |
| 6,762,036 | B2 | | 7/2004 | Farb et al. |
| 6,773,595 | B2 | | 8/2004 | Gantzer |
| 7,198,940 | B2 | * | 4/2007 | Vellinger et al. ......... 435/286.5 |
| 7,390,648 | B1 | | 6/2008 | Palacios-Boyce |
| 7,435,870 | B2 | | 10/2008 | Serbedzija et al. |
| 2001/0039045 | A1 | | 11/2001 | Chan et al. |
| 2003/0151735 | A1 | | 8/2003 | Blumenfeld et al. |
| 2003/0190744 | A1 | | 10/2003 | McGarry et al. |
| 2005/0266547 | A1 | | 12/2005 | Scherze et al. |
| 2007/0117131 | A1 | | 5/2007 | Groner |

FOREIGN PATENT DOCUMENTS

DE    4443902 C1    4/1996

(Continued)

OTHER PUBLICATIONS

"U.S. Appl. No. 10/528,056, Advisory Action mailed Apr. 20, 2009", 3 pgs.

(Continued)

Primary Examiner—Herbert J. Lilling
(74) Attorney, Agent, or Firm—Schwegman, Lundberg & Woessner, P.A.

(57) ABSTRACT

The invention relates to a method for cultivating cells of the most diverse type, particularly human or animal cells. According to the invention, a culture is prepared from cells of at least one specified type in a defined environment, and the cells of the relevant culture are supplied with assigned, liquid nutrient media, growth factors, gases and the like. A combination of the following method steps is provided: a) preparing at least one cell culture inside at least one cell culture chamber (20) of a cell culture system (30); b) starting a flow of freely selectable, liquid media into the at least one cell culture chamber (20) in order to continuously supply the at least one cell culture; c) starting a flow of different gases with freely selectable concentrations into the at least one cell culture chamber (20) in order to effect a constant and continuous gassing of the at least one cell culture; d) effecting a regulated or controlled heating of the at least one cell culture chamber (20) in such a manner as to ensure a constant temperature therein over the duration of an experiment; e) carrying out permanent microscopic observation of the at least one cell culture inside the at least one cell culture chamber (20) without removing samples of the cell culture over the duration of an experiment, and; f) permanently measuring all relevant cell culture parameters using corresponding sensors that are integrated inside the at least one cell culture chamber (20).

14 Claims, 2 Drawing Sheets

FOREIGN PATENT DOCUMENTS

Figure 1:
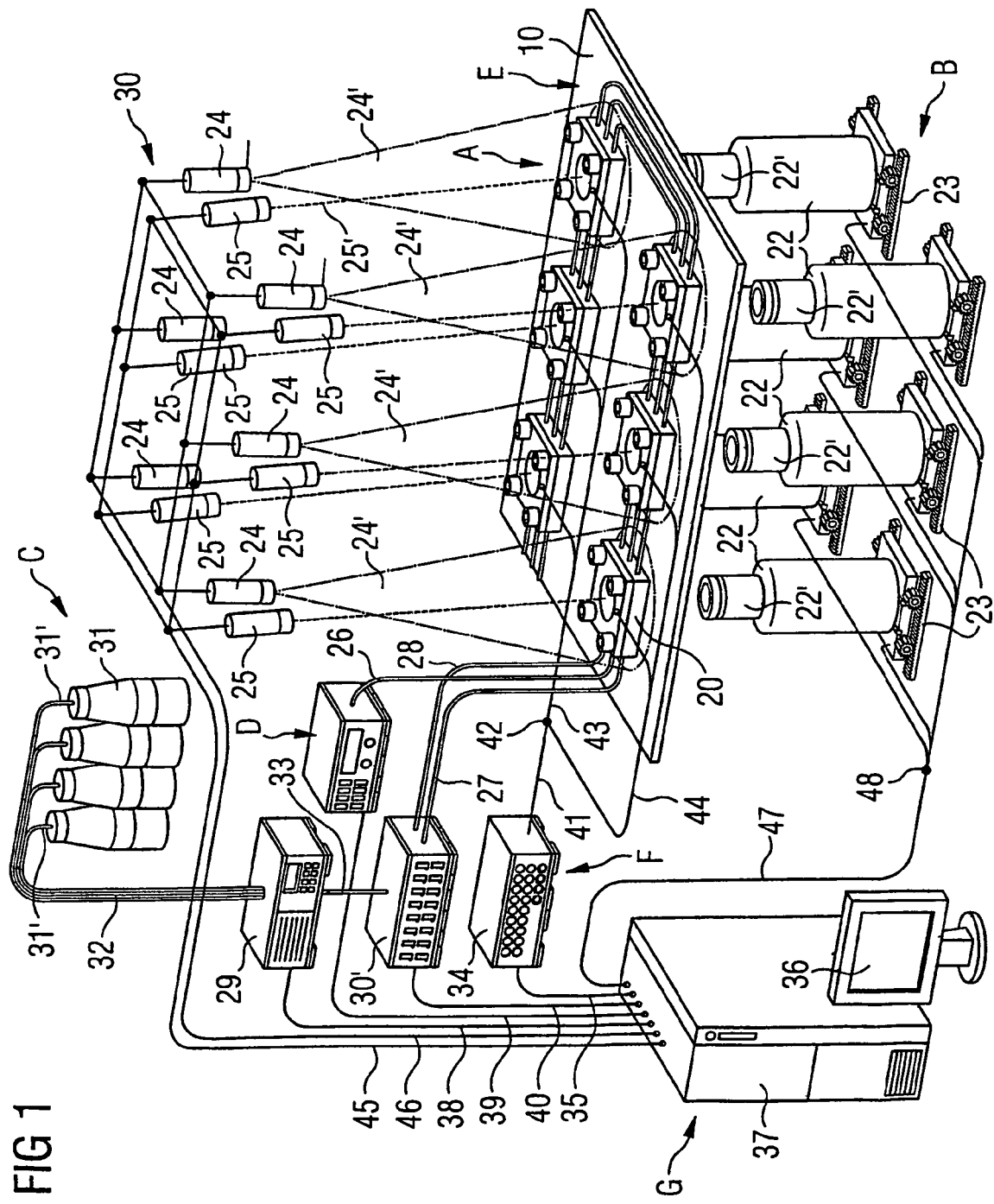

| | | |
|---|---|---|
| DE | 19915178 | 10/2000 |
| EP | 0224800 A2 | 6/1987 |
| EP | 0999266 A1 | 5/2000 |
| GB | 2341611 A | 3/2000 |
| WO | WO-93/18132 A1 | 9/1993 |
| WO | WO-97/37001 A1 | 10/1997 |
| WO | WO-98/17822 A1 | 4/1998 |
| WO | WO-99/23206 A1 | 5/1999 |

OTHER PUBLICATIONS

"U.S. Appl. No. 10/528,056, Non-Final Office Action mailed Jun. 25, 2009", 11 pgs.

"U.S. Appl. No. 10/528,056, Non-Final Office Action mailed Jul. 24, 2008", 10 pgs.

"U.S. Appl. No. 10/528,056, Final Office Action mailed Jan. 23, 2009", 11 pgs.

"U.S. Appl. No. 10/528,056, Response filed Apr. 9, 2009 to Final Office Action mailed Jan. 23, 2009", 10 pgs.

"U.S. Appl. No. 10/528,056, Response filed May 11, 2009 to Advisory Action mailed Apr. 20, 2009 and Final Office Action mailed Jan. 23, 2009", 10 pgs.

"U.S. Appl. No. 10/528,056, Response filed Oct. 24, 2008 to Non-Final Office Action mailed Jul. 24, 2008", 9 pgs.

"U.S. Appl. No. 10/528,058, Advisory Action mailed Oct. 1, 2008", 3 pgs.

"U.S. Appl. No. 10/528,058, Final Office Action mailed Jun. 26, 2009", 13 pgs.

"U.S. Appl. No. 10/528,058, Non-Final Office Action mailed Jan. 6, 2009", 15 pgs.

"U.S. Appl. No. 10/528,058, Non-Final Office Action mailed Feb. 14, 2008", 9 pgs.

"U.S. Appl. No. 10/528,058, Final Office Action mailed Jun. 23, 2008", 8 pgs.

"U.S. Appl. No. 10/528,058, Preliminary Amendment filed Mar. 15, 2005", 2 pgs.

"U.S. Appl. No. 10/528,058, Response filed Apr. 6, 2009 to Non Final Office Action mailed Jan. 6, 2009", 12 pgs.

"U.S. Appl. No. 10/528,058, Second Amendment and Response filed May 12, 2008 to Non-Final Office Action mailed Feb. 14, 2008", 48 pgs.

"U.S. Appl. No. 10/528,058, Response filed Nov. 24, 2008 to Final Office Action mailed Jun. 23, 2008 and Advisory Action mailed Oct. 1, 2008", 8 pgs.

"European Application No. 02779357.9, Office Action mailed Jan. 26, 2007", 2 pgs.

"European Application No. 02779357.9, Office Action mailed May 29, 2006", 3 pgs.

"European Application No. 02779357.9, Office Action mailed Jul. 22, 2005", 2 pgs.

"European Application No. 02779357.9, Reply filed Nov. 29, 2005 to Office Action mailed Jul. 22, 2005", 7 pgs.

"European Application No. 02779357.9, Reply filed Mar. 7, 2007 to Office Action mailed Jan. 26, 2007", 1 pg.

"German Application No. 10128810.7, Examination Report dated Jan. 31, 2007", 3 pgs.

"International Patent Application Serial No. PCT/EP02/10358, International Preliminary Examination Report dated Apr. 11, 2005", (w/ English Translation), 10 pgs.

"International Patent Application Serial No. PCT/EP02/10358, international Search Report mailed Jan. 2, 2003", 6 pgs.

Beksaç, M., et al., "An Artificial Intelligent Diagnostic System on Differential Recognition of Hematopoietic Cells From Microsopic Images", *Cytometry*, 30(5), (1997), 145-150.

Boland, M. V., et al., "Automated recognition of patterns characteristic of subcellular structures in fluorescence microsopy images", *Cytometry*, 33(3), (1998), 366-375.

Cai, X. Y., et al., "Micro-pattern recognition using a microscope coherent optical processor (M-COP)[IC inspection]", *Third International Conference on Holographic Systems, Components and Applications*, (1991), 226-230.

Camisard, V., et al., "Inline Characterization of Cell Concentration and Cell Volume in Agitated Bioreactors Using In Situ Microscopy: Application to Volume Variation Induced by Osmotic Stress", *Biotechnology and Bioengineering*, 78(1), (2002), 73-80.

Dubois, F., et al., "Pattern Recognition with a Digital Holographic Microscope Working in Partially Coherent Illumination", *Applied Optics*, 41(20), (2002), 4108-4119.

Firestone, L. M., et al., "Continuous Class Pattern Recognition for Pathology, With Applications to Non-Hodgkin's Follicular Lymphomas", *Pattern Recognition*, 29(12), (1996), 2061-2078.

Machemer, H., et al., "Gravikinesis in *Paramecium*: Theory and isolation of a Physiological response to the natural gravity vector", *Journal of Comparaive Physiology A*. vol. 168, (1991), 1-12.

Minuth, W. W., et al., "Orango-typical environment for cultured cells and tissues <Organ-spezifisches Environment fur kultivierte Zellen und Gewebe>", *BIOforum*, 17, (1994), 412-416.

Ong, S. H., et al., "Image Analysis of Tissue Sections", *Computers in Biology and Medicine*, 26(3), (1996), 269-279.

* cited by examiner

METHOD FOR CULTIVATING CELLS, PARTICULARLY HUMAN OR ANIMAL CELLS

CROSS REFERENCE TO RELATED APPLICATIONS

This application is the US national phase of PCT application PCT/EP2002/010357 filed Sep. 16, 2002.

The invention relates to a method of cultivating cells of the most diverse type, particularly human or animal cells; one culture each is prepared from cells of at least one specific type in a defined environment and the cells of the relevant culture are supplied with assigned, liquid nutrient media, growth factors, gases or the like in the process.

In general, cultures of the above-mentioned type are prepared on the basis of individual cells that either result from parts of tissue, primary cultures, from cell lines or cell stems obtained by enzymatic, mechanic or chemical disintegration.

With previously known cell cultivation methods, culture vessels made of plastic that are incubated in $CO_2$ incubators are used for preparing the cultures. This guarantees a constant temperature (e.g. 37° C.) and a buffering of the medium by way of a 5 to 10 percent $CO_2$ gassing. Oxygen supply is effected by simple diffusion. With the known methods and equipment for the cultivation of cells, co-cultivation and freely changeable incubation conditions are normally not possible.

For microscopic observation or for specific examinations, the culture vessels have to be taken out of the relevant incubators, whereby incubation is interrupted, the cells cool down and the test conditions are no longer constant as a result.

The previously known methods for the cultivation of cells, however, do no longer meet the requirements of modern cell culture technology.

With regard to current main research areas in the pharmaceutical industry in particular, these being the fields of inflammation (rheumatics), the fight against cancer, cardiovascular diseases, Aids, apoptosis (programmed cell death) and blood coagulation, the development and the testing of suitable new active agents and drugs by means of a new method for cultivating cells that enables the testing of substances and actions under almost in-vivo conditions, that means with an almost perfect mapping of complex, biological systems before passing on to the clinical phases (tests on test persons) is indispensable.

Out of consideration for the above-mentioned situation, there is demand for a method of simulating the progress of reactions within one or several organ system(s) (e.g. by means of a series connection of cell culture chambers with hepatocytes and other types of cells, testing for degradation products and metabolites) in order to considerably minimize, on the one hand, the period of time that passes between the identification of the action of a substance and drug approval and to enable the obtaining of necessary findings on the mechanism of action of the substance within a complex biological system before passing on to the clinical test phase, on the other hand.

A similar situation is given, for example, in the area of cosmetics industry as well.

State-of-the-art technology includes, for example, multivalent cell culture systems (see DE 199 15 178 A1, for example), problem-adapted cell culture systems for specific tasks (see WO 98/17822, for example) or methods for the replication of cell cultures (see WO 97/37001 for example).

Furthermore it is known from WO 99/23206 that there is a method for mixing a cell culture infected with varicella in cylindrical bottles, for example.

Finally a method and a device used to take up a cell culture are known from EP 0 999 266 A1; these aim at creating the most homogenous possible conditions for the molecular biological or genetic examination of cells.

Out of consideration for the situation in the field of modern cell culture technology described in the beginning, the target of the present invention is now to create a new, improved method of cultivating cells of the most diverse type, particularly human or animal cells, that does away with the disadvantages of the previously known methods and offers, in particular, the opportunity to simulate highly complex, biological process in real time and under almost in-vivo conditions (i.e. like in a living organism), the ultimate goal being the realization of a computer-controlled process flow.

The task defined above is solved on the basis of a method of cultivating cells of the most diverse types, particularly human or animal cells, one culture each of cells of at least one specific type being prepared in a defined environment and the cells of the relevant culture being supplied with assigned, liquid nutrient media, growth factors, gases and the like, according to the invention by a combination of the following process steps:

a) Preparing of at least one cell culture inside at least one cell culture chamber of a cell culture system;

b) Starting a flow of freely selectable, defined liquid media into the at least one cell culture chamber in order to continuously supply the at least one cell culture;

c) Starting a flow of different gases with freely selectable concentrations into at least one cell culture chamber in order to effect a constant and continuous gassing of the at least one cell culture;

d) Effecting a regulated or controlled heating of the at least one cell culture chamber in such a manner as to ensure a constant temperature therein over the duration of an experiment;

e) Carrying out a permanent microscopic observation of the at least one cell culture inside the at least one cell culture chamber without removing samples of the cell culture over the duration of an experiment; and f) Permanently measuring all relevant cell culture parameters using corresponding sensors that are integrated inside the at least one cell culture chamber.

As far as the method according to the invention is concerned, the relevant number of cell cultures is preferentially placed simultaneously inside a predefined number of cell culture chambers und then the further process steps as defined above are carried out.

Here the cell culture chambers may either be connected in series or in parallel.

The method of cultivating cells according to the invention ensures in particular that the cells of all cultures are continuously supplied with liquid nutrient media, growth factors, gases or the like, without cells of a culture having to be taken out of their habitual, defined environment, while all cell cultures can be permanently examined under the microscope without the gassing having to be interrupted.

According to a further embodiment of the method according to the invention, the type of liquid media and/or their directions of flow and/or their distribution and/or their flow volumes may be varied over the duration of an experiment, but the types of gas and/or their directions of flow and/or their distribution and/or the gassing concentrations may be varied as well; this results ultimately in the fact that the method according to the invention can be configured in an extremely flexible manner.

In particular, if cell culture chambers of a cell culture system have been connected in series, the liquid media can be continuously passed on from cell culture chamber to cell culture chamber.

Accordingly, gases can also be continuously passed on from cell culture chamber to cell culture chamber.

In order to ensure constant temperatures in the individual cell culture chambers over the duration of an experiment for the method of cultivating cells according to the invention, the temperatures inside the individual cell cultures are measured continuously and entered into a corresponding temperature adjustment circuit and/or temperature control circuit as actual temperature values so that the heating of the individual cell culture chambers can be adjusted and/or controlled accordingly.

As will be explained in more detail below, each cell culture chamber is fitted with its own heating for this purpose, while one infrared temperature measuring device each is fitted above the relevant cell culture chamber; this device measures the temperature in the relevant cell culture and reports this measured temperature value to a monitoring and control system. If the temperature that was preset at the beginning changes in the at least one cell culture chamber, the temperature adjustment and/or control circuit reduces or increases the heating power of the heating of the relevant cell culture chamber. However, temperatures can also be measured using other temperature sensors.

As will be explained in more detail below as well, the temperatures in the individual cell culture chambers can be freely adjusted and changed by means of the monitoring and control system over the entire duration of an experiment for reasons of flexibility.

A further, particularly advantageous embodiment of the method provides that one cell culture each of different types is prepared inside at least one cell culture chamber on both sides of a gas-permeable membrane installed there for the purpose of a direct co-cultivation of both cell cultures.

This kind of co-cultivation is preferably carried out in such a way so as to supply the cells growing on the one side of the membrane, that means on the apical side, by a first flow of media, whereas the cells of the second cell culture growing on the other side of the membrane, that means on the basolateral side, are supplied by way of second flow of media that differs from the first flow of media. In this way, the cells on the apical side act as a covering layer, while the cells on the basolateral side act as interior cells. The cells of the first cell culture and the cells of the second cell culture are in a relatively close contact to each other via the membrane so that it is possible to examine exchange processes inside the layers on the apical side and on the basolateral side.

Furthermore it is also possible to examine a potential exchange of effective, bio-active molecules (e.g. growth factors, hormones, etc.) in the course of such a co-cultivation if gas-permeable membranes with different, selectable pore sizes are used. These kinds of examinations are particularly important for parts of tissue consisting of different types of cells, such as the transition endothelium cells-fibroblasts (blood vessels) or mucous membrane cells-fibroblasts (intestine, stomach).

Furthermore there is another, particularly advantageous embodiment of the method in application of the method according to the invention for an indirect co-cultivation that provides that different biological systems (i.e. types of tissue/cells) are connected in series in suitable cell culture chambers. In that way, it is possible to reproduce, so to say, complete organ systems and to examine the relevant. metabolic processes. These measures can be explained in more detail using an example: A substance that is normally not toxic is absorbed via the digestive tract and gets into the liver via the bloodstream. The liver cells catabolize the substance into catabolic products that may have a toxic effect under certain circumstances. In order to check this, the "suspect" substance is placed in an incubation chamber that is populated with hepatocytes (liver cells). Via a defined nutrient media supply (media flow="blood vessel"), possibly toxic catabolic products get into a cell culture chamber that is connected to it; when nerve cells, for example, die off there, it can be inferred that the substance is neurotoxic.

A further, extremely advantageous embodiment of the method according to the invention provides for a video-supported microscopic observation of the at least one cell culture in the at least one cell culture chamber; this will also be described in more detail below.

The method according to the invention can also be further developed in such a way so as to transfer all data that are obtained By a permanent microscopic observation of the at least one cell culture inside the at least one cell culture chamber and/or By a permanent measuring of the relevant cell culture parameters and/or By a permanent measuring of the temperature in the at least one cell culture inside the at least one cell culture chamber to a computer-controlled monitoring and control system for further processing there.

The permanent measuring of the relevant cell culture parameters is carried out by means of a software-aided measuring method here in particular.

A continuous measuring of cell culture parameters can be carried out preferably by means of specific probes and/or sensors, for example for pH values, lactate, electric potential and the like; these measurements can be evaluated and presented by means of a suitable software. This type of measurement achieves more exact results than conventional methods, and this enables you to analyze certain questions that cannot be analyzed with measuring methods used up to now. For example, certain tests on animals in the pre-clinic phase can be replaced for the most part by means of such a software-aided measuring method.

Figure 2:
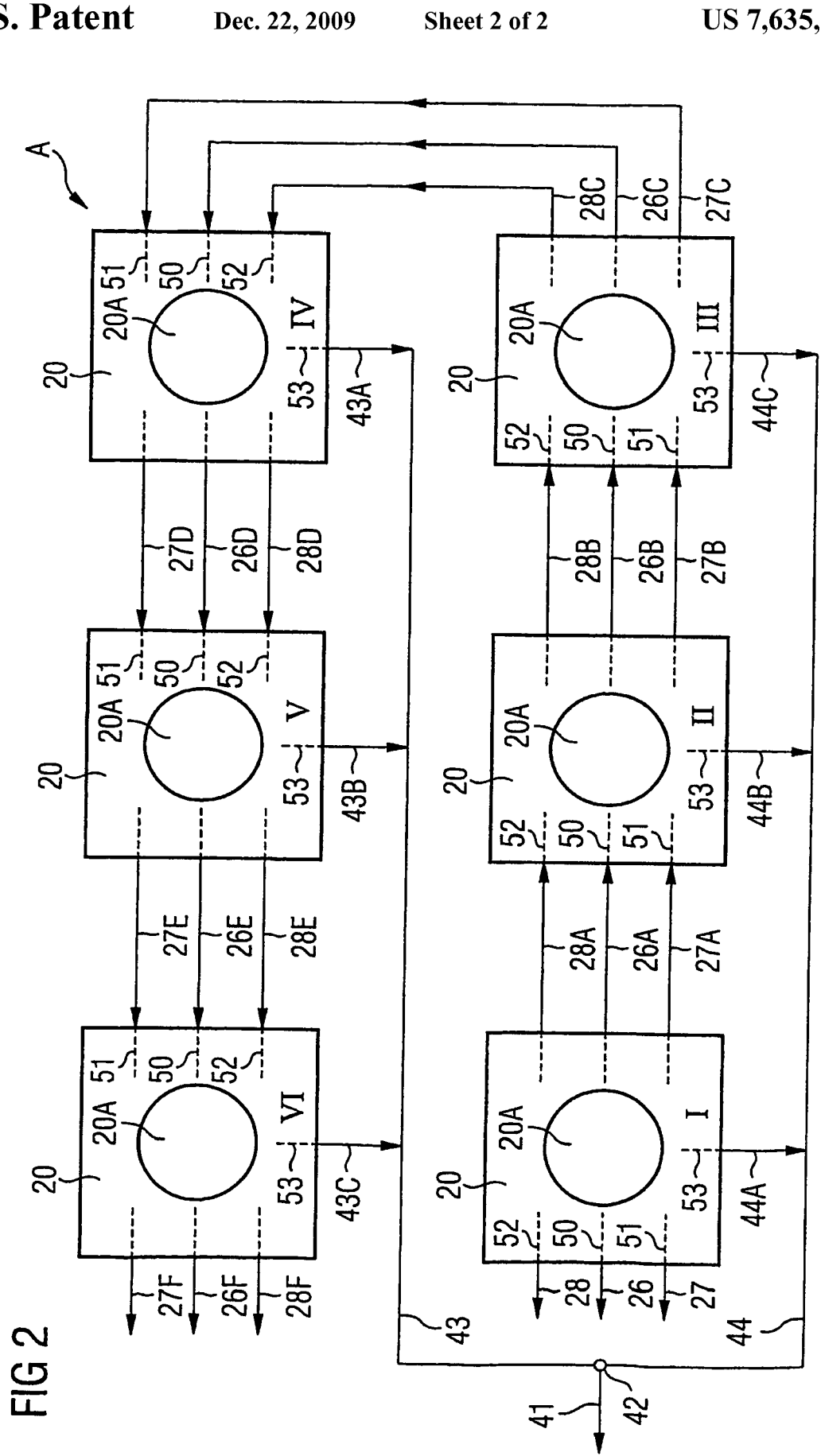

Now the invention is explained in more detailed in the following on the basis of application examples:

FIG. 1 showing a diagram of a complete, closed cell culture system for which a pre-defined number of cell culture chambers is used and that serves to apply the method of cultivation of cells according to the invention; and FIG. 2 showing a diagram of the cell culture chambers connected in series of the cell culture system presented in FIG. 1.

FIG. 1 shows a closed cell culture system 30 in which, for example, six cell culture chambers 20 have been positioned as group A on a base 21 that has been assigned accordingly. In particular, the base 21 constitutes a heating system E for incubation that ensures constant temperatures inside each of the cell culture chambers 20 of the cell culture chamber group A during the operating time of the cell culture system 30.

This heating system E is preferably used to provide for an electric heating of the relevant cell culture chamber 20; this enables a very exact temperature control. This heating system E is in particular designed in such a way that each individual cell culture chamber 20 of the cell culture chamber group A disposes of a separate heating that is integrated in the base 21.

It is particularly advantageous that the heating system E can be controlled via an assigned software. For this purpose, a system of infrared temperature measuring devices 25 is fitted above the cell culture chamber group, each individual cell culture chamber 20 being assigned a corresponding infrared temperature measuring device 25. The relevant infrared temperature measuring device 25 reads the temperature in the cell culture by means of an infrared beam 25' emitted from the relevant cell culture chamber 20 and permanently reports the relevant measuring result to a computer-controlled monitoring and control system G that mainly consists of a data processing system 37 and an accessory monitor 36. The individual infrared temperature measuring devices 25 are connected to the monitoring and control system G via a joint connecting line 45. When the initially pre-set temperatures in the cell culture chambers 20 of the cell culture chamber group A change, the heating system E is controlled and/or adjusted automatically via the monitoring and control system G, this means that the temperature in the individual cell culture chambers 20 is permanently adjusted to a constant temperature.

It would also be possible to measure the temperature in the individual cell culture chambers 20 by means of other temperature sensors instead of infrared temperature measuring devices 25.

Furthermore it is possible to use the software contained in the monitoring and control system to ensure that the temperatures in the individual cell culture chambers 20 of the cell culture chamber group A can be freely set and selected over the duration of the entire experiment if this becomes necessary for specific reasons.

For the purpose of a permanent, video-supported, microscopic observation of the inside of the relevant cell culture chamber 20, a video system B with an accordingly assigned microscope system is provided. This video system B will be explained in more detail in the following.

Below every individual cell culture chamber 20 of the cell culture chamber group A that includes a total of six cell culture chambers in this application example, a video camera 22 with a microscope adapter 22' is fitted on a mechanically adjustable, mobile table, therefore there is a total of six video cameras 22 with accessory microscope adapters 22'. Thus one video camera 22 each with a microscope adapter 22' serves to observe one cell culture chamber 20 each. After the experiment has been started and after meaningful areas in the cell culture contained in the relevant cell culture chamber 20 have been identified, an observation sector in the cell culture chamber 20 is determined. The mechanically adjustable mobile table 23 is moved to this observation sector then by means of adjusting screws (not represented), then the mobile table 23 is locked and the video system B remains in the same position over the entire duration of the experiment as a result. Furthermore the definition setting at the relevant microscope adapter 22' is adjusted at the start of the test. This adjustment process on the relevant microscope adapter 22' is carried out for all six cell culture chambers 20 and then remains unchanged until the experiment has been completed.

The video system B is preferably controlled via the software contained in the monitoring and control system G as well. Every individual video camera 22 with microscope adapter 22' is controlled in the process. This is carried out in particular in such a way that pictures of the relevant cell culture in the cell culture chamber 20 are taken at freely selectable intervals (every minute, for example), a light source 24 fitted above the relevant cell culture chamber 20, illuminating the relevant cell culture at the relevant point in time at which such a recording is made, so that a sufficient illumination of the inside of the cell culture chamber 20 is ensured for the video recordings. When the video recording is completed, the control switches the relevant light source 24 into a weak, dimmed-out standby state until the next video recording is made. The light beam and/or light cone that is emitted by each of the light sources 24 and that enters into the relevant cell culture chamber 20 through a suitable pane of glass (not represented) is marked 24' in FIG. 1.

All light sources 24 are connected to the monitoring and control system G via a joint connecting line 46.

Every single light beam/light cone 24 illuminates the entire area of the cell culture contained in the relevant cell culture chamber 20.

The video system B is also connected to the monitoring and control system G via a line 47; from the monitoring system, the line 47 is connected to a junction point 48 to which the individual video cameras 22 are connected via correspondingly assigned lines.

The video system B with microscope system as described above is only one of the possible models. Another possible embodiment of such a system for the permanent observation of the inside of the cell culture chambers comprises a single observation system, consisting of a video camera and a microscope adapter, and is installed on a mobile table; this mobile table moves to the six cell culture chambers 20 of the cell culture chamber group A at freely selectable intervals. The adjustment of the observation system is carried out for the individual cell culture at the start of the test, this means preferably after meaningful areas have been identified in the relevant cell culture, by means of the respective software included in the monitoring and control system G, this means that the six target positions of the moving table on which the observation system has been mounted are programmed by means of the respective computer program. On account of the mechanic tolerances of the moving table, however, it is necessary to make recordings of an area that is larger than the area inside the individual cell culture chamber 20 to be observed. The software now serves to define the area to be observed within this larger area. The software is able to record and to recognize contours, this means that the contours and the configuration of the cells is recognized when the table moves in the direction of a cell culture chamber again and an initially defined observation area is recorded.

This observation system that has been explained last is not represented in detail in the drawings, but the individual cell culture chambers 20 are also illuminated by means of the light sources 24, as it has already been explained in detail above.

Furthermore the cell culture system 30 represented in FIG. 1 is equipped with a dosage system C for liquids (e.g. liquid nutrient media and the like) that is fitted with e.g. four liquid storage tanks 31 with one assigned liquid take-off line 31' each; these liquid take-off lines 31' constitute a group of lines 32. This group of lines 32 is, on the other hand, connected to a pump system 29 through which the different cell culture chambers 20 of the cell culture chamber group A are supplied with freely selectable liquids that are contained in the liquid tanks 31.

The pump system 29, on the other hand, is connected to a multi-valve module 30' via a line 33. The liquids are supplied to the cell culture chamber group A from the multi-valve module 30' via sterile hose line systems 27 and 28; these liquids are passed on from the individual cell culture chambers 20 in a flexible manner, this means from one cell culture chamber to the next. The liquid supply as well as the passing on of liquids is carried out via sterile hose systems that are installed with standard hose connecting elements and distributors at the start of a test; this means that they are connected to corresponding supply channels of a relevant cell culture chamber 20. Here the connection of the standard hose elements (not represented in detail in the drawings) with the assigned supply channels of the relevant cell culture chamber is adjusted in such a way that sterility is guaranteed.

For reasons of flexibility, the types of liquids and/or the directions of flow and/or the distribution of liquids and/or their flow volumes can be changed and/or controlled during a test; this is preferably controlled by the computer-controlled monitoring and control system G. For this purpose, the pump system 29 is connected to the monitoring and control system G via a connecting line 38 and the multi-valve module 30' via a connecting line 40.

Therefore the dosage system C of the cell culture system 30 enables you to supply the cell culture chamber group A with a variety of different liquids.

Furthermore the cell culture system 30 is equipped with a gassing system D for a variety of different gases. This gassing system D serves to gas the different cell culture chambers 20 of the cell culture chamber group A with a variety of different gases, e.g. air, $O_2$, $N_2$, $CO_2$. From the gassing system D, the gas is supplied to the cell culture chamber group A via a sterile hose line 26. Here the gases can be passed on from the different cell culture chambers 20 in a flexible manner as well, this means from one cell culture chamber to the next by means of accordingly assigned supply channels.

The gas is altogether supplied and passed on via sterile tubes that are installed by means of standard hose connecting elements and distributors at the start of a test. The connections of the hose connecting elements with the correspondingly assigned supply channels of a relevant cell culture chamber 20 are adjusted in such a way so that sterility is guaranteed. With the gassing system D as well, the types of gases and/or the directions of flow and/or the gas distribution and/or the gassing concentration can be changed and/or controlled during an experiment for reasons of flexibility. For this purpose, the gassing system D, on the other hand, is connected to the monitoring and control system G that contains the relevant software for controlling the gassing system D via a connecting line 39.

Finally the cell culture system 30 further includes a monitoring system F with predefined sensor modules 34. By means of this monitoring system F, the relevant parameters in the relevant cell culture chamber 20 of the cell culture chamber group A can be measured, measured permanently in particular, using accordingly assigned sensors, for the entire duration of a test, these parameters being, for example, pH value, glucose, lactate, oxygen, electric potential, etc. For this purpose, the monitoring system F is connected to the individual cell culture chambers 20 of the cell culture chamber group A of the cell culture system 30 via a line 41, via a junction point 42 and from there via further lines 43 und 44 and accordingly assigned branch lines.

The parameters measured by the sensors (not shown) are transmitted by the monitoring system F via a line 35 to the computer-controlled monitoring and control system G for further processing.

Each cell culture chamber 20 is equipped with corresponding sensor connecting channels; this will be explained in detail below. The sensors and the relevant assigned channels are adjusted to each other in such a way so as to guarantee sterility.

A particularly advantageous design of the monitoring system F in connection with the computer-controlled monitoring and control system G enables a permanent measuring of the relevant cell culture parameters by means of a software-aided-measuring method (as already explained above).

FIG. 2 shows a schematic top view of the cell culture chamber group A of the cell culture system according to FIG. 1. With this cell culture chamber group A, a total of six cell culture chambers 20 is connected in series, so to speak, in such a way that the liquid media as well as the gases can be passed on from one cell culture chamber 20 to the next, this means can be passed on continuously to the relevant subsequent cell culture chamber 20.

In each of the six cell culture chambers 20, at least one cell culture to be examined is established; for the sake of simplicity, however, this example of application will be based on six cell cultures the relevant cells of which have to be supplied with defined liquid nutrient media, growth factors, gases and the like.

For this purpose, a flow of freely selectable, defined, liquid media, on the one hand, and a flow of different gases with freely selectable concentrations, on the other hand, to the six cell culture chambers 20 of the cell culture chamber group A is started; as already explained above, the liquids are primarily supplied to the cell culture chamber group A from the multi-valve module 30' according to FIG. 1 via the sterile tube line systems 27 and 28, while the gas is supplied to the cell culture chamber group A from the gassing system D according to FIG. 1 via the sterile hose line 26 at the same time.

For reasons of clarity, the six cell culture chambers 20. that are subsequently connected in series are marked I, II, III, IV, V and VI.

The hose line systems 27 and 28 for liquids and the hose line 26 for gases are directly connected to the first cell culture chamber 1; the result is that the hose line 26 directly discharges into a gas channel 50 inside this first cell culture chamber, whereas the hose tube system 27 discharges into a corresponding liquid channel 51 and the hose line system 28 discharges into a liquid channel 52 inside this first cell culture chamber I at a time. In this way, the cell culture contained in the first cell culture chamber I is supplied with liquid media and gases, and then the subsequent cell culture chambers II to VI are correspondingly supplied with liquid media and gases successively. In detail, the cell culture chamber I is connected, via the liquid hose lines 27A and 28A and via a gas hose line 26A, to the second cell culture chamber II, that is again connected, via the liquid hose tubes 27B and 28B and a gas hose line 26B, to the third cell culture chamber m, that is again connected, via the liquid hose tubes 27C and 28C and a gas hose tube 26C, to the fourth cell culture chamber IV, that is again connected, via the liquid hose lines 27D and 28D as well as a gas hose line 26D to the fifth cell culture chamber V, that is finally connected, via the liquid hose lines 27E and 28E and via a gas hose line 26E, to the sixth cell culture chamber VI.

On account of this connection of the six cell culture chambers 20 in series, each liquid hose line 28A or 28B or 28C. or 28D or 28E discharges into a liquid channel 52 each inside every cell culture chamber, each liquid hose line 27A or 27B or 27C or 27D or 27E respectively discharges into a corresponding liquid channel 51 inside every cell culture chamber, whereas every gas hose line 26A or 26B or 26C or 26D or 26E respectively discharges into a corresponding gas channel 50 of every cell culture chamber.

From the sixth cell culture chamber VI, the liquid outlet lines 27F and 28F and a gas outlet line 26F branch off.

As a result, all cell cultures inside the six cell culture chambers I to VI can be continuously supplied with freely selectable, defined, liquid media as well as subjected to a constant, continuous gassing via the gassing system D according to FIG. 1, as already explained in detail above.

Please note that FIG. 2 only shows one of many possible directions of flow for liquids and gases.

By means of the flexible hose line systems for liquids and gases explained above, other cell culture chamber combinations than the ones shown in FIG. 2 can be controlled as well.

Another particularly important aspect is that the cell culture chamber group A as a whole is permanently connected to the monitoring system F according to FIG. 1, so that all relevant parameters can be measured in the relevant cell culture chamber 20 by means of accordingly assigned sensors for the entire duration of a test. For this reason, each of the cell culture chambers 20 is fitted inside with a corresponding channel 53 for the connection of sensors. In detail, the first cell culture chamber I is connected, via a line 44A, the second cell culture chamber II, via a line 44B, and the third cell culture chamber III, via a line 44C, to a line 44, while the fourth cell culture chamber IV is connected via a line 43A, the fifth cell culture chamber V, via a line 43B, and the sixth cell culture chamber VI, via a line 43C, to a line 43. The lines 43 and 44 lead to a junction point 42 that is connected, via a line 41, to the monitoring system F according to FIG. 1.

The sensors that are arranged inside each cell culture chamber 20 and that are not represented in detail here enable a permanent measuring of the relevant parameters; the relevant measured values are then transmitted by the monitoring system F to the computer-controlled monitoring and control system G according to FIG. 1 for further processing.

FIG. 2 further shows that the top of every cell culture chamber 20 of the cell culture chamber group A is fitted with a round window 20A with a glass pane; this enables illumination of the entire area of the cell culture contained in the relevant cell culture chamber 20, as it has already been explained in detail by means of FIG. 1 above.

As for the rest, the cell culture chamber as such is the subject matter of a German patent application of the same applicant with the designation "Cell culture chamber for a cell culture system" (official application Ser. No. 10/528,058).

The method of cultivating cells according to the invention offers, in particular, the opportunity to simulate highly complex, biological processes in real time and almost under in-vivo conditions.

A special advantage of the method according to the invention is that it can be used, in particular, to investigate cellular functions, to examine the action of drugs, to develop drugs, to co-cultivate different types of cells and parts of tissue, to carry out organotypic studies, to observe tumor cells in a typical environment or to carry out toxicological studies.

The invention claimed is:

1. A method for cultivating human or animal cells, one culture each of cells of at least one specific type being established in a defined environment and the cell cultures being supplied with assigned, liquid nutrient media, growth factors, and gases, the method comprising:
    establishing at least two different types of cell cultures inside at least one cell culture chamber of a cell culture system, wherein two of the cell cultures, each of a different type, are established on a single gas-permeable membrane within the at least one cell culture chamber for a direct co-cultivation of both cell cultures, wherein one of the two of the cell cultures is established on a first side of the gas-permeable membrane, and the other of the two of the cell cultures is established on a second side of the gas-permeable membrane;
    starting a flow of freely selectable, defined, liquid media in the at least one cell culture chamber in order to ensure a continuous supply for the at least two cell cultures;
    starting a flow of different gases with freely selectable concentrations into the at least one cell culture chamber in order to ensure a constant, continuous gassing of the at least two cell cultures;
    heating the at least one cell culture chamber in a regulated or controlled manner so as to ensure a constant temperature there over the duration of an experiment;
    continuously microscopically observing at least one of the cell cultures inside the at least one cell culture chamber, without samples of the cell culture being taken over the duration of an experiment, wherein continuous microscopic observation is performed using a camera including a microscope attachment, the camera being disposed on a displaceable table for movement of the camera with respect to the cell culture chamber;
    moving the camera with respect to the cell culture chamber while programming movement positions of the camera; and
    continuously measuring cell culture parameters selected from the group consisting of pH values, lactate values and electric potential relevant to treating inflammation, cancer, cardiovascular disease, AIDS, relevant to programmed cell death, or relevant to blood coagulation, using sensors integrated in the at least one cell culture chamber.

2. The method according to claim 1, wherein at least one of a type of liquid media, the flow directions thereof, the distribution thereof, or the flow volumes are varied over the duration of an experiment.

3. The method according to claim 1, wherein, when cell culture chambers are connected in series, the liquid media are continuously passed on from cell culture chamber to cell culture chamber.

4. The method according to claim 1, wherein a type of gases, the flow directions thereof, the distribution thereof, or the gassing concentrations are varied over the duration of an experiment.

5. The method according to claim 1, comprising starting a first flow of media to one side of the membrane, namely, the apical side with the first cell culture, and starting a second flow of media that differs from the first flow of media to the other side of the membrane, namely, the basolateral side, with the second cell culture.

6. The method according to claim 1, comprising connecting different biological systems in series in corresponding cell culture chambers.

7. The method according to claim 1, wherein the continuous measuring of the relevant cell culture parameters includes software-aided measuring of the relevant cell culture parameters.

8. The method according to claim 1, wherein the continuous microscopic observation includes:
    automatically determining cell contours during movement of the camera;
    automatically storing the determined cell contours on the computer software; and
    automatically recognizing those stored determined cell contours when the camera again moves past the cell culture chamber later on during the observation.

9. The method according to claim 1, wherein a given number of cell culture chambers is established, these cell culture chambers being connected in series.

10. The method according to claim 1, wherein a given number of cell culture chambers is established, these cell culture chambers being connected in parallel.

11. The method according to claim 9, wherein, when cell culture chambers are connected in series, the gases are continuously passed on from cell culture chamber to cell culture chamber.

12. The method according to claim 1, wherein the temperature prevailing in the at least two cell cultures within the at least one cell culture chamber is measured continuously and input as an actual temperature value into a corresponding temperature adjusting circuit or control circuit to enable a corresponding adjustment or control of the heating of the cell culture chamber.

13. The method according to claim 1, comprising a video-supported microscopic observation of the at least two cell cultures in the at least one cell culture chamber.

14. The method according to claim 1, comprising transmitting to a computer-controlled monitoring and control system data obtained by at least one of the continuous microscopic observation of the at least two cell cultures within the at least one cell culture chamber, the continuous measuring of the relevant cell culture parameters, or the continuous measuring of the temperature in the at least two cell cultures inside the at least one cell culture chamber, wherein the computer-controlled monitoring and control system is used to process the data.

* * * * *

UNITED STATES PATENT AND TRADEMARK OFFICE
CERTIFICATE OF CORRECTION

PATENT NO. : 7,635,575 B2  Page 1 of 1
APPLICATION NO. : 10/528060
DATED : December 22, 2009
INVENTOR(S) : Scherze et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 374 days.

Signed and Sealed this

Twenty-first Day of December, 2010

David J. Kappos
*Director of the United States Patent and Trademark Office*